United States Patent [19]

Koehler

[11] Patent Number: 4,556,679

[45] Date of Patent: Dec. 3, 1985

[54] EARTHWORM IRRITANT

[76] Inventor: Peter L. Koehler, 7 Bevell La., North Syracuse, N.Y. 13212

[21] Appl. No.: 688,877

[22] Filed: Jan. 4, 1985

Related U.S. Application Data

[63] Continuation-in-part of Ser. No. 574,719, Jan. 30, 1984, abandoned.

[51] Int. Cl.$^4$ ............................................. A01N 27/00
[52] U.S. Cl. ........................................ 514/764; 424/84
[58] Field of Search ................... 424/356, 84; 514/764

[56] References Cited

U.S. PATENT DOCUMENTS 4,177,288  12/1979  Gohlke ................................ 424/304

OTHER PUBLICATIONS

The Merck Index; 8th Edition (1968); Nonoxynol Pseudocumene.

Chemical Abstracts, vol. 97 (1982); #105599h; Kumiai, "Tetrachloroisophthalonitrile Emulsion".

Primary Examiner—Leonard Schenkman
Assistant Examiner—Joseph A. Lipovsky
Attorney, Agent, or Firm—Bruns and Wall

[57] ABSTRACT

An improved earthworm irritant composition that is highly effective in causing worms to leave their holes during the day time or at night and come to the surface. The composition is mixed with a relatively large amount of water and then poured on the ground, and the effectiveness of the composition is at least in part due to its slow rate of evaporation. The composition of the invention is a liquid and it is essentially comprised of 1,2,4-trimethylbenzene, which is the irritating agent, and a nonionic surfactant which enables the 1,2,4-trimethylbenzene to mix thoroughly with the water that is added.

1 Claim, No Drawings

EARTHWORM IRRITANT

RELATED APPLICATION

This application is a continuation-in-part of a co-pending application Ser. No. 574,719, filed Jan. 30, 1984, now abandoned by Peter L. Koehler for EARTHWORM IRRITANT.

BACKGROUND OF THE INVENTION

This invention relates generally to the procurement of earthworms for fishing bait, and has particular reference to an improved chemical composition that causes worms to leave their holes and come to the surface of the ground where they can easily be picked up.

Compositions for inducing earthworms to come out of the ground so that they can be collected for bait have been marketed heretofore. Such compositions contain a substance that is a minor irritant or agitant to the worms and makes them want to get above ground. Normally, the prepared composition is mixed with water and spread on the ground, and as it sinks in, the worms begin to surface. The applicant is not aware of any patent that is directed to a composition or formulation of this nature.

The only prior art that the applicant is aware of are two publication excerpts cited in the prosecution of co-pending application Ser. No. 574,719, supra. These are: "The Merck Index", 8th Edition (1968), Nonoxynol & Pseudocumene; and "Chemical Abstracts", Vol. 97 (1982), #105599h, Kumiai, Tetrachloroisophthalonitrile Emulsion. In the "Merck Index", Nonoxynol is defined on page 745 and Pseudocumene is defined on page 883 and no relationship between the two is suggested. Also, in the "Merck Index" the nonionic surfactant formulas given are not the same as the nonionic surfactant formula of the invention.

The Kumiai abstract very briefly states that the fungicide TPN is readily emulsified by using pseudocumene as a solvent. The abstract further states that a compound containing TPN5, pseudocumene 80, and a surfactant of 15% is given. This differs from the present invention which is a formulation for an earthworm irritant rather than a fungicide composition. More important, however, is the fact that in Kumiai the TPN is the active ingredient whereas in the invention disclosed herein, the pseudocumene (1,2,4-trimethylbenzene) is the active ingredient.

SUMMARY OF THE INVENTION

The present invention provides an improved earthworm irritant composition that is highly effective in causing worms to leave their holes and come to the surface both in the day time and at night. The composition is mixed with a relatively large amount of water and then poured on the ground, and the effectiveness of the composition is at least in part due to its slow rate of evaporation. This permits the mixture to act for a longer period of time and penetrate farther into the ground. The mixture is not injurious to the worms or to the grass or ground on which it is spread.

The composition of the invention is a liquid and it is essentially comprised of 1,2,4-trimethylbenzene, which is the irritating agent, and a nonionic surfactant which enables the trimethylbenzene to mix thoroughly with the water that is added. Small amounts of aromatic and coloration materials are included in the composition.

DESCRIPTION OF THE PREFERRED EMBODIMENT

The earthworm irritant composition disclosed herein is essentially comprised of 1,2,4-trimethylbenzene in the range of 70-94% and a nonionic surfactant in the range of 29-5%. The remainder of the composition—approximately 1%—is made up of scented adjuvants and coloration materials. The trimethylbenzene and the surfactant are mixed together under conditions of ambient temperature and pressure to produce a simple solution.

The 1,2,4-trimethylbenzene is the worm irritant or agitating agent. It is an isomer of mesitylene and hemimellitene, and is commercially available under the trademark "Pseudocumene" from the Koch Chemical Company of Corpus Christi, Tex. The nonionic surfactant that is employed is sold under the registered trademark "IGEPAL" by GAF Corporation of New York, New York.

The GAF Corporation markets a series of "IGEPAL" CO nonionic surfactants and the one that is employed in the composition of the invention is "IGEPAL" CO-630. All of the "IGEPAL" CO surfactants are derived from the same hydrophobic starting material, nonylphenol. By increasing the amount of hydrophilic substance, ethylene oxide, combined with the nonylphenol, a series of different products each with a different hydrophobic—hydrophilic balance is obtained. For "IGEPAL" CO-630 the mole ratio "n" is 9, the ethylene oxide is 65% and the HLB is 13.0, where the HLB is the hydrophilic—lipophilic balance.

In using the composition of the invention, 5 milliliters (a teaspoonful) of the composition is thoroughly mixed with five gallons of water and the mixture is spread as uniformly as possible on the ground, as by pouring it from a watering can. Stated another way, the mixture can consist of one part of the irritant composition to 3100 parts of water. This mixture will normally cover approximately 1200–1400 square inches of ground, and shortly after it has been applied it can be expected from extensive testing that 15 to 20 worms will surface. Normally worms surface only at night but the irritant composition of the invention causes them to surface in the broad daylight.

EXAMPLE

In a commercial formulation, 85% by volume of 1,2,4-trimethylbenzene ("Pseudocume" from Koch Chemical Company) was thoroughly mixed with 14% by volume of a nonionic surfactant ("IGEPAL" CO-630 from GAF Corporation, as described above). To this mixture was added a scented adjuvant in the form of a pine scent oil (marketed by Berje of Long Island City, N.Y.) and coloration (sold under the name "Pylam Solvent Blue #203841" by Pylam Products Co., Inc. of Garden City, N.Y.), the adjuvant and coloration totalling approximately 1% by volume. The adjuvant masks a slight odor in the mixture while the coloration contributes to an attractive appearance. The ingredients were mixed together under conditions of ambient temperature and pressure, and the mixture was then bottled for distribution.

In a test use of the above irritant formulation, one part of the formulation was thoroughly mixed with 3100 parts of water and this mixture was spread evenly over the ground using a watering can. The mixture covered approximately 1200–1400 square inches of ground and within a few minutes seventeen worms surfaced. The mixture was not harmful to the skin of the worms nor did it do any damage to the grass or ground over which it was spread.

As noted hereinbefore, the composition disclosed is particularly effective in inducing worms to surface day or night because of its irritating action and relatively slow rate of evaporation. This slow rate permits the mixture to act over a longer time span and also enables the mixture to penetrate farther into the ground. In this connection, it should be noted that while water alone, as in a rainfall, will to some extent induce worms to surface, actual tests show that the composition of the invention produces a significantly larger number of surfaced worms in a like time period. The composition is particularly well adapted for collecting nightcrawlers but it can also be utilized for collecting any other kind of worm.

From the foregoing description it will be apparent that the invention provides a novel and very advantageous composition for procuring worms for fishing bait during the day time or at night. As will be understood by those familiar with the art, the invention may be embodied in other specific forms without departing from the spirit or essential characteristics thereof.

I claim:

1. A composition for inducing earthworms to come out of the ground so that they can be easily collected for bait, said composition having a relatively slow evaporation rate and consisting essentially of approximately 85% by volume of 1,2,4-trimethylbenzene and approximately 14% by volume of a nonionic surfactant, the surfactant being comprised of approximately 35% nonylphenol and approximately 65% ethylene oxide.

* * * * *